United States Patent [19]

Maly et al.

[11] 4,435,080

[45] Mar. 6, 1984

[54] ARRANGEMENT FOR MEASUREMENT OF DYNAMIC PROPERTIES OF MICROPARTICLES

[76] Inventors: Zdenek Maly, Nationalstrasse 7, Kreuzlingen CH-8280, Switzerland; Vladislav Blazek, Konradinstr. 2, Munich D-8000, Fed. Rep. of Germany

[21] Appl. No.: 264,983

[22] Filed: May 18, 1981

[30] Foreign Application Priority Data

May 23, 1980 [CH] Switzerland ............... 4084/80

[51] Int. Cl.³ ............... G01N 21/85; G01N 21/53
[52] U.S. Cl. ............... 356/426; 356/337
[58] Field of Search ............... 356/426–428, 356/337, 39

[56] References Cited

U.S. PATENT DOCUMENTS 3,733,136  5/1973  Porath-Furedi ............... 356/427
3,955,890  5/1976  Bessis et al. ............... 356/39

Primary Examiner—Bruce Y. Arnold
Attorney, Agent, or Firm—Bachman and LaPointe

[57] ABSTRACT

The disclosure teaches a device for measuring the dynamic properties of microparticles including at least two flat measuring bodies or discs spaced from each other, with the distance therebetween being adjustable and the space therebetween being filled with a suspension of microparticles to be measured. At least one of said bodies or discs is movable so that a defined magnitude of fluid shear stress is generated in the suspension. The device also includes means for passing a light beam through both bodies and said suspension so that, during rotation and when rotation is stopped, different diffraction patterns are generated. Means for measuring the diffraction patterns is also included thereby obtaining useful data concerning the dynamic properties of the microparticles.

8 Claims, 10 Drawing Figures

ARRANGEMENT FOR MEASUREMENT OF DYNAMIC PROPERTIES OF MICROPARTICLES

This invention relates generally to the measurement of dynamic properties of microparticles and, more particularly, to the measurement of their deformability and internal viscoelasticity, respectively.

In the past, different methods have been used to measure the deformability of microparticles.

(a) One of these methods involves filtration of a microparticle suspension through a grid with calibrated holes whose diameter is less than the dimensions of the microparticles. The ratio between the number of transited and non-transited particles serves as a measure of their deformability. The drawbacks of this method are as follows: It is impossible to repeat the measurement with the same sample of microparticles. It is also impossible to measure a relaxation time constant, which gives important data about the internal viscoelasticity of the microparticles. The relaxation time constant is the time interval during which the particles retain their previous form when force applied on them is removed.

(b) Another of these methods involves deformation of microparticles due to application of centrifugal forces, followed by a fixation of microparticles in the deformed state. The drawbacks of this method are the same as in the previous case. Another shortcoming is that only individual microparticles are measured and therefore it is time consuming to gather the data about the whole population of microparticles.

(c) Another of the methods involves elongation of a microparticle, fixed at one point, due to force of fluid flow. This method has the same drawbacks as (a) and (b), when we do not take into account the difficulties connected with the arrangement of such experiment.

(d) Another of these methods involves elongation of a microparticle, which is sucked into a micropipette by a defined force. This method has been used especially for measurement of cell membrane properties. The drawbacks are the same as (c).

(e) Another of these methods involves deformation of microparticles and the measurement of this deformation with the aid of a so called concentric viscometer. This device consists of two concentric cylinders, the gap between which is filled with a dilute suspension of microparticles and the coherent light beam passing through it generates a diffraction pattern. These patterns at various speeds of rotation of one of the cylinders, and hence various values of applied fluid shear stress, are recorded and analyzed, see M. Besis and N. Mohandas, Blood Cells 1 (1975), 307-313. There are several limitations of this arrangement. Light rays, passing through the surfaces of the cylinders, are refracted. This effect leads to the generation of intensive vertical strip of light in the diffraction pattern. Difficulties exist, connected with changing of samples, while new adjustment of the optical system is needed after every change of sample. Also, there are problems with cleaning. The possibility of sedimentation of microparticles in the solution and the gap between cylinders cannot be changed without changing of the cylinders.

Accordingly, it is an object of this invention to overcome the above mentioned limitations. Therefore the measuring arrangement must allow the following features (a) Measurement of the dynamic properties of microparticles, that is, their deformability, elongation, relaxation constant etc., when a wide range of shear stress values is applied on these particles.

(b) Repetition of the measurement with the same group of microparticles when conditions of the measurement are changed either continuously or stepwise. This measurement must be possible during every phase of the operation.

(c) Changing the operation conditions without the need either to rebuild the arrangement or to change the analyzed suspension.

(d) A simple and quick change of analyzed samples.

(e) Elimination of the sedimentation of microparticles.

(f) Use of such a detection system, which enables a graphical or/and mathematical representation of data.

SUMMARY OF THE INVENTION

The object, features, and advantages of this invention will become evident from the following detailed description of the manner and mode of practicing the invention.

The measuring arrangement, which is the subject of this invention, includes two flat discs or measuring bodies, the gap between which is filled with a suspension of microparticles. In one embodiment, one of the discs is movable, while the other is fixed. A fluid shear stress is generated in the suspension due to rotation of the disc. The magnitude of the stress depends on the speed of the disc rotation, on the viscosity of the suspension and on the width of the gap between both discs. The microparticles are forced to change their shape or dimension due to the fluid shear stress. The magnitude and kind of deformation is a measure of elastic properties of the microparticles. When a beam of coherent light, e.g. laser light, is passed through the suspension, diffraction of the light occurs and a corresponding diffraction pattern is generated. Alterations of the microparticle shape are followed by corresponding changes of the diffraction pattern. An analysis of these changes can enable one to gain quickly and simply data about the dynamic properties of the particles. Other embodiments are shown in the drawings and described in the instant specification.

BRIEF DESCRIPTION OF THE DRAWINGS

The present invention will be more readily understood with the aid of the drawing wherein.

DETAILED DESCRIPTION

The following examples are included as being merely illustrative and are not to be considered as limiting the scope of the invention in any manner.

Figure 1:
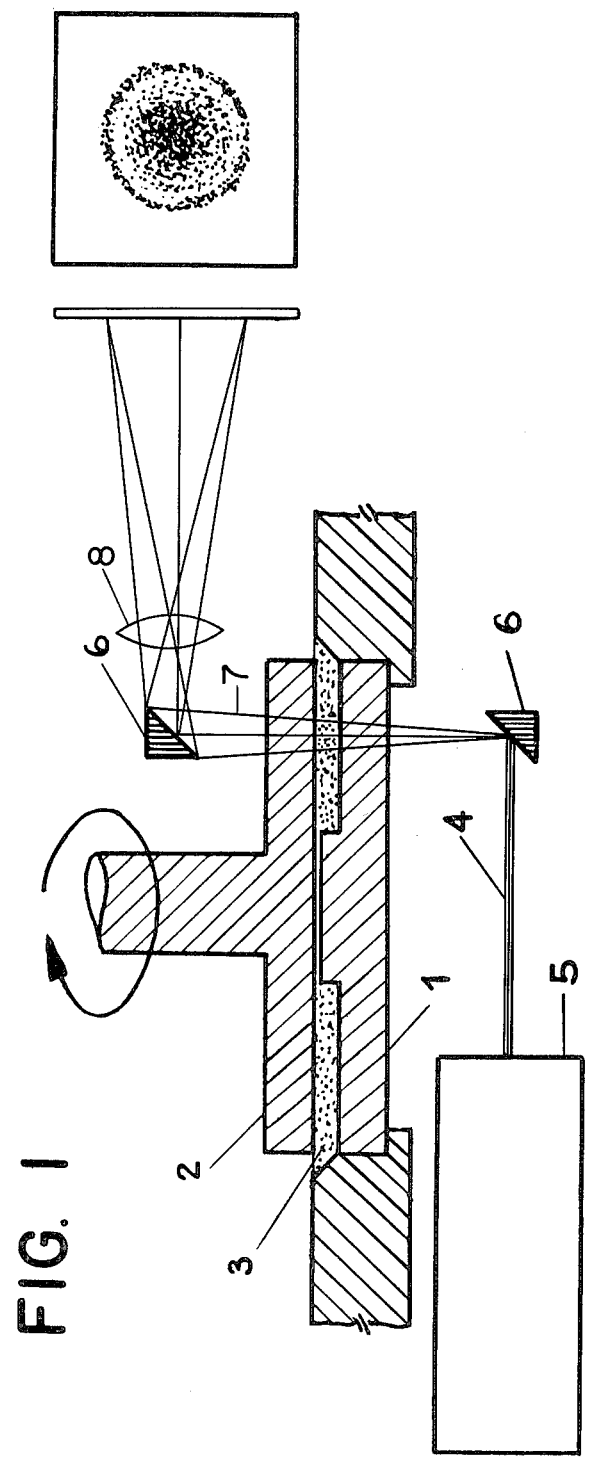
FIG. 1 represents a partially schematic representation of the device of the present invention.

FIG. 1 is a schematic of the measuring arrangement. The adjustable gap between the fixed disc (1) and movable, rotating disc (2) is filled with a suspension of microparticles (3). A parallel beam of coherent light (4), generated by the laser (5), is passed through the system and is reflected either by prisms or plane mirrors (6).

The light is diffracted (7) due to presence of the microparticles in the suspension. An optical system consists of a convergent lens (8). The basic principle of this lens is to collect the plane waves emerging from the object at different angles, and to focus these waves in the back focal plane of the lens (8). Such an optical system makes it possible to obtain the image of the diffraction pattern at a finite distance from the object illuminated with a parallel beam of light. In the back focal plane of the lens (8) the diffraction pattern can be detected and analyzed. The detection can be provided by optoelectronic detectors.

Figure 2:
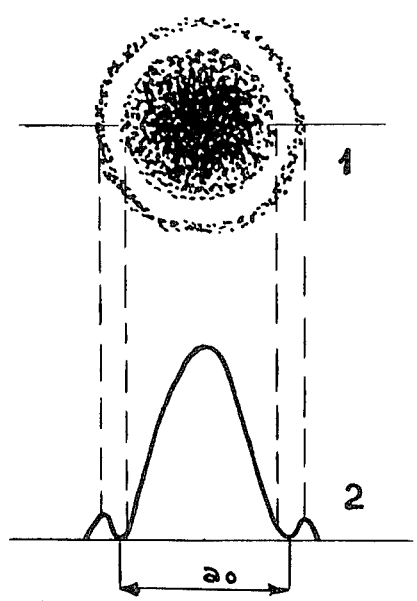
FIGS. 2 and 3, respectively, represent diffraction patterns on a suspension of human red cells when no fluid stress is applied in the cells and when fluid shear stress according to the present invention is applied on the cells.
Figure 3:
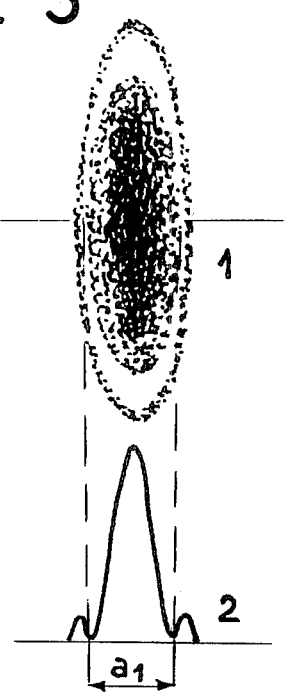

The diffraction patterns, generated due to light diffraction on the suspension of human red cells, are demonstrated in FIG. 2 and FIG. 3, respectively. FIG. 2 represents the diffraction pattern (1), when no fluid shear stress is applied on the cells, i.e. without rotation of the disc, and also the corresponding distribution of light intensity in the diffraction plane (2). FIG. 3 shows the diffraction pattern (1), when fluid shear stress is applied on the cells, i.e. the disc is rotated and also the corresponding distribution of light intensity in the diffraction plane (2). The cell deformability is calculated with the aid of the following formula:

$$d/d_o = a_o/a_l$$

where d denotes the elongation of the cells and $d_o$ denotes their diameter.

The following examples represent the different arrangement of measuring bodies and their different forms:

EXAMPLE I

Figure 4:
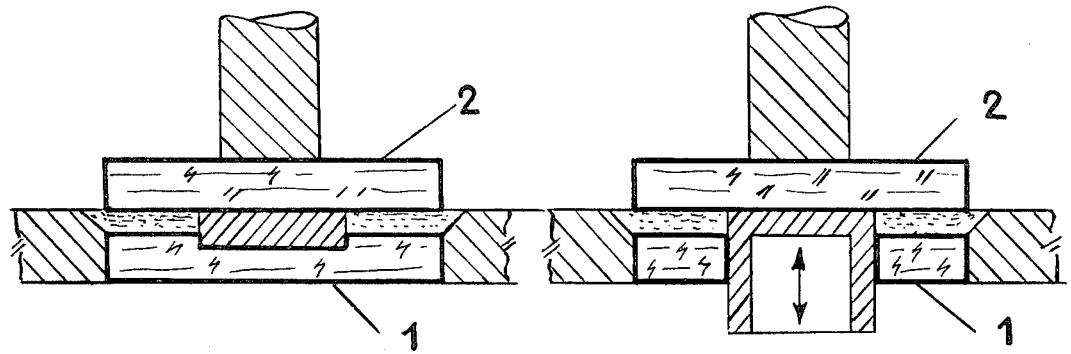
FIGS. 4-7, inclusive, represent alternate embodiments, partially schematic, of the device of the present invention.

The measuring system shown in FIG. 4 consists of two round discs, where one of them (1) (e.g. under one) is fixed and the other one (2) (e.g. upper one) can be rotated. The distance between both discs is held constant with the aid of some supporting element, whose thickness is either constant or can be regulated. The discs or their corresponding parts must be transparent for light.

EXAMPLE II

Figure 5:
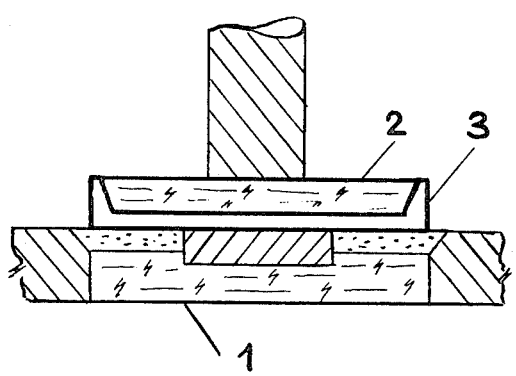
Figure 5A:
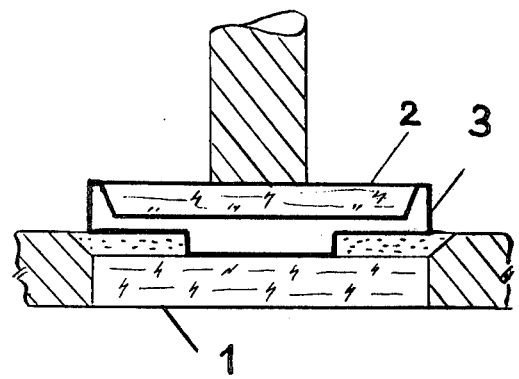

The measuring system shown in FIG. 5 consists of the base plate (1), the rotating disc (2) and one interchangeable element (3) which may be a small plate or dish. Either the same supporting element as in Example I is used to keep the distance between both discs constant, or the element (3) is joint together with the supporting element (FIG. 5a). This arrangement helps to make the cleaning more easier.

EXAMPLE III

Figure 6:
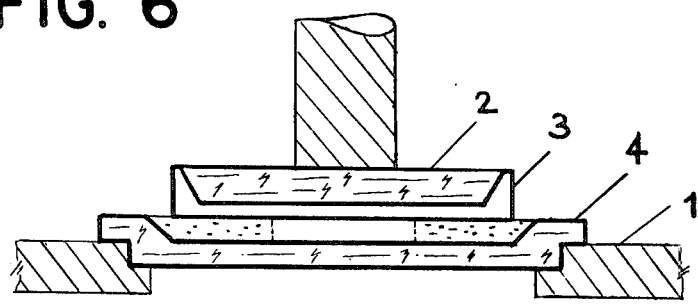
Figure 6A:
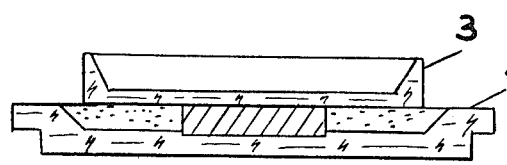
Figure 6B:
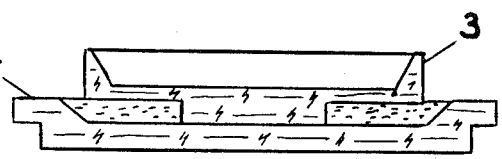

FIG. 6 represents a measuring arrangement, which is appropriate when more samples are to be measured. The base plate (1) and also rotating disc (2) are equipped with the interchangeable elements (3) and (4). The interchangeable supporting element (FIG. 6a) or fixed one (FIG. 6b) is used for keeping the distance between both discs constant. This arrangement is very useful when many serial measurements are to be done. Many sorts of microparticles are deformable immediately when the fluid shear stress is applied on them. Therefore the linear motion of the measuring body can be used in this case.

EXAMPLE IV

Figure 7:
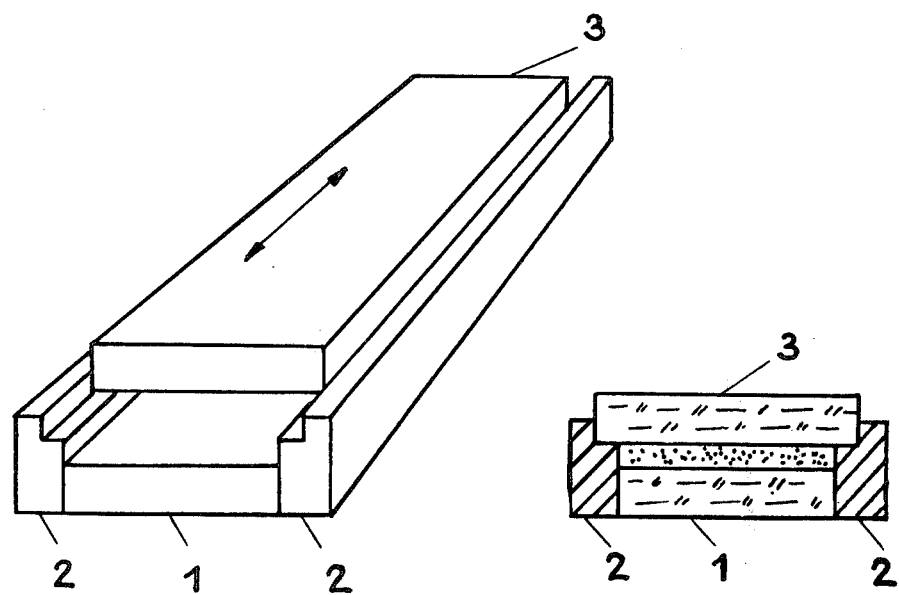

FIG. 7 represents a measuring arrangement, where the linear motion of the measuring body is used. It consists of the base plate (1), the supporting elements (2) and the movable plate (3). The speed of movement of the plate (3) can be controlled.

There has been disclosed certain preferred embodiments of this invention, but also another measuring arrangements are possible, without departing from the spirit and scope of this invention as defined in the appended claims.

We claim:

1. A device for measuring the dynamic properties of microparticles which comprises: at least two flat measuring bodies spaced from each other, with the distance therebetween being adjustable and the space therebetween being filled with a suspension of microparticles to be measured, wherein at least one of said bodies is movable so that a defined magnitude of fluid shear stress is generated in the suspension; means for passing a light beam through both bodies and said suspension so that during rotation and when rotation is stopped different diffraction patterns are generated; and means for measuring said diffraction patterns, thereby extracting useful data concerning the dynamic properties of the microparticles.

2. A device according to claim 1 wherein one measuring body is fixed.

3. A device according to claim 1 wherein said measuring bodies are discs.

4. A device according to claim 1 wherein both measuring bodies are rotating in the same direction but with different speeds of rotation.

5. A device according to claim 1 wherein both measuring bodies are rotating in opposite directions.

6. A device according to claim 1 wherein at least one measuring body is removable and can be changed before every measurement is done.

7. A device according to claim 1 wherein both measuring bodies are removable and can be changed before every measurement is done and the distance therebetween is fixed.

8. A device according to claim 1 wherein said measuring bodies are transparent for light, either permanently or for a specific time interval.

* * * * *